United States Patent [19]
Merrifield et al.

[11] 3,956,428
[45] May 11, 1976

[54] AMINE PHOSPHITES

[75] Inventors: D. Bruce Merrifield, Williamsville;
Joseph A. Pawlak, Cheektowaga;
James G. Colson, Williamsville, all of N.Y.

[73] Assignee: Hooker Chemicals & Plastics Corporation, Niagara Falls, N.Y.

[22] Filed: June 6, 1975

[21] Appl. No.: 584,446

Related U.S. Application Data

[63] Continuation of Ser. No. 326,200, Jan. 24, 1973, abandoned.

[52] U.S. Cl. ............... 260/929; 260/45.9 R; 260/928; 260/936; 260/945
[51] Int. Cl.² .............. C07F 9/141; C07F 9/145
[58] Field of Search ........... 260/945, 944, 928, 929

[56] References Cited
UNITED STATES PATENTS 3,172,871  3/1965  Malz et al. .................... 260/944 X

*Primary Examiner*—Richard L. Raymond
*Attorney, Agent, or Firm*—Peter F. Casella; William J. Crossetta, Jr.

[57] ABSTRACT

Compounds of the formula

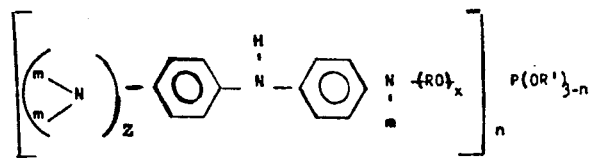

wherein
R is selected from the group consisting of ethylene, 1,2 propylene, 1,2 butylene, 2,3 butylene, styrylene and mixtures thereof,
$x$ is an integer from 1 to 12,
R' is substituted or unsubstituted alkyl or aryl,
$n$ is an integer from 1 to 3,
each $m$ is a member, selected independently from the group consisting of hydrocarbon of 1 to 20 carbon atoms, $-(RO)_x$-, $-(RO)_x$H and $(-(RO)_x)_n P(OR')_{3-n}$,
wherein R, R', $n$ and $x$ are as above described, providing where $m$ is $-(RO)_x$-, the O— bond thereof is attached to the phosphorus of an adjacent P(OR') moiety of a common nitrogen, and
$z$ is 0 or 1, providing that when $z$ is

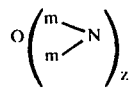

is hydrogen, are disclosed having utility as non-staining antioxidants.

10 Claims, No Drawings

AMINE PHOSPHITES

This is a continuation of application Ser. No. 326,200, filed Jan. 24, 1973, now abandoned.

BACKGROUND OF THE INVENTION

Ideally, any antioxidant for organic substrates such as rubber or other plastic material, whether providing protection in the presence of atmospheric oxygen, ozone or any other oxidant, should not introduce objectionable characteristics into the substrate which make it hazardous to handle, more subject to premature curing or weaker physically. The antioxidant should prevent oxidative attack over extended periods of time without volatilization or change in visual appearance of the organic substrate caused by staining or change in color as by frosting as well as cracking or cutting of the subsrate surface.

Antioxidants for use in any substrate subject to change induced by either chemical or physical action ideally prevent that change for extended time periods without adversely affecting the properties of the substrate. Any composite effect derived from the use of a single antioxidant such as combined heat, light, aging, oxidation and flex cracking stability, extend the general applicability of that antioxidant.

Although attack on carbon-carbon unsaturation by ozone may be generically considered oxidation of the substrate, the intermediate ozonides and/or hydroperoxides present a unique problem which is not solved by antioxidants generally. Thus, antiozonants are a special group of antioxidants which in themselves may or may not be functional toward attack by atmospheric oxygen.

The function of ozone in initiating cracking of rubber has been studied extensively since 1945. Various antiozonants have been discovered which extend the useful life of rubber exposed to ozone by extending the time for initial cracking and retarding the extent of cracking in rubber. Many commercial antiozonants are derived from the N-substituted paraphenylene-diamines.

Those N-substituted para-phenylenediamines prepared by alkylating para-aminodiphenylamine with a ketone such as the 4-isopropylamino diphenylamine are effective antiozonants and do not cause premature curing or retard the curing rate when used in rubber. However, the 4-alkylaminodiphenylamines are colored and stain the rubber in which they have been incorporated.

Conventionally, antioxidants are introduced into rubber in the latex stage. A solid antioxidant is dispersed in the latex to provide a dispersion approaching as closely as possible a homogeneous mixture while liquid antioxidants are mixed with the latex by emulsification. At this point, it is very important that the antioxidant not affect premature coagulation of the rubber or cause creaming of the latex (rubber destabilization and separation from water in the latex). After introduction of the antioxidant, the rubber is coagulated to separate it from the water as an elastomeric dry material. The rubber appears as small agglomerated masses which are dried by hot air to form crumbs of rubber. Another addition of antioxidant is conventionally made to the crumb or to compressed crumb rubber during milling, extruding or other fabrication treatments.

BRIEF DESCRIPTION OF THE INVENTION

In accordance with this invention, there is provided a group of antidegradants of the formula

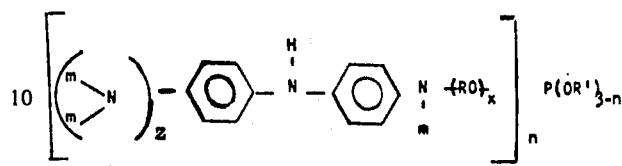

wherein
R is selected from the group consisting of ethylene, 1,2 propylene, 1,2 butylene, 2,3 butylene, styrylene and mixtures thereof,
x is an integer from 1 to 12,
R' is substituted or unsubstituted alkyl or aryl,
m is an integer from 1 to 3,
each m is a member independently selected from the group consisting of hydrocarbon of 1 to 20 carbon atoms, $-(RO)_{\overline{x}}$, $-(RO)_{\overline{x}}H$ and $(-(RO)_{\overline{x}})_n$ $P(OR')_{3-n}$; wherein R, R' and x are as above described, providing where m is $-(RO)_{\overline{x}}$, the O—bond thereof is attached to the phosphorus of an adjacent P(OR') moiety of a common nitrogen, and
z is 0 to 1, providing that when z is

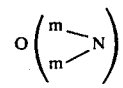

Z is hydrogen.

A preferred mode of the invention are those compounds wherein R' is aryl selected from the group consisting of phenyl and substituted phenyl or lower alkyl of 1 to 18 carbon atoms.

The novel antioxidants of this invention are particularly useful when incorporated into polyolefin compositions such as polyethylene, polypropylene, polybutylene, polybutadiene, poylstyrene and copolymers thereof. The polyolefins generally posses molecular weights above 1,000 extending upwards into and including molecular weights of 1,000,000. The polyolefin may be of the high density, medium density or low density type. The polyolefin stabilized with the antioxidants of this invention are useful as coating materials as well as thermoplastic molding compounds. Polyethylene compositions containing the antioxidants of this invention are particularly useful as insulators or condensors in electronic equipment.

The compounds of this invention may be used to stabilize lubricants, either the synthetic or petroleum based greases and oils, including the aliphatic esters, polyalkylene oxides, silicones, phosphoric acid esters, silicic acid esters, polyfluorinated hydrocarbons, and the like. Lubricant oils of petroleum origin with which the antioxidants of this invention may be incorporated, include the motor oils, transmission oils, cutting oils, hydraulic oils, and the like, known in the industry.

The compounds of this invention may be incorporated into synthetic greases such as the alkali metal, alkaline earth and aluminum base greases in solid or semi-solid form.

Furthermore, the compounds of this invention may be added to motor fuels that contain saturated and unsaturated blends of hydrocarbon materials.

Throughout the remaining portion of the disclosure, the discussion and exemplification of the use of the compounds of this invention is made with specific reference to styrene-butadiene rubber. It is to be understood that for the purpose of preventing oxidation either from atmospheric oxygen or ozone, the compounds of this invention may be used in a manner known to the stabilizing art for the protection of organic materials, such as waxes and synthetic resins, as well as natural rubber, and especially with the synthetic rubbers of which styrenebutadiene rubber (SBR) and nitrile rubber are exemplary.

The staining types of styrene-butadiene rubber generally contain para-phenylenediamine type antioxidants, conventionally applied in from 0.2 to about 2.5 parts per 100 parts of rubber. Surprisingly, the compounds of this invention, although derived from the staining type antioxidants are non-staining or so slightly staining so as to produce negligible discoloration in the rubber product. Thus, the excellent antiozonant, antioxidant stabilizing properties of the para-phenylenediamine type antidegradants are extended into the non-discloring field of application by the compounds of this invention.

The antioxidants of this invention may be employed to produce dispersions or emulsions which are mixed with rubber latex during coagulation and protect this latex during subsequent treatment.

The compounds of this invention need not be added to styrene-butadiene rubber in the latex stage but are also applicable as antioxidants when added to the rubber crumb or baled crumbs at the mill or other fabrication stage. Thus, the compounds of this invention may be incorporated into an oxidizable organic substrate, such as styrene-butadiene rubber, in an amount from about 0.01 to about 5 parts per 100 parts of substrate, to afford non-staining to slightly staining compositions with improved stability toward oxidation by atmospheric oxygen and ozone.

DETAILED DESCRIPTION OF THE INVENTION

The compounds of this invention represent phosphite esters of oxy alkylenated-aminodiphenylamines. The amine components of the ester are produced by known techniques such as is disclosed in U.S. Pat. No. 3,330,777. Generally, the aminodiphenylamine reactant is oxyalkylenated with ethylene oxide, propylene oxide, 1,2-butylene oxide, 2,3-butylene oxide or styrene oxide to introduce hydroxy alkyl groups to the free amino groups thereby producing a tertiary amine. With the introduction of a basic catalyst and an additional amount of the alkylene oxide reactant, the chain length of the N-hydroxyalkylated group may be extended to afford a tertiary amine derivative, containing up to about 12 repeating alkoxy groups with a terminating hydroxyl group.

The oxyalkylenated-aminodiphenylamine intermediate is subsequently transesterified with a trialkyl or triaryl phosphite so as to replace part or all of the aryl or alkyl groups on the phosphite with an oxyalkylated amine. The transesterification may be carried out at atmospheric, sub-atmoshperic or super atmospheric pressures at temperatures in the range of about 25° centigrade to about 300° centigrade.

EXAMPLE 1

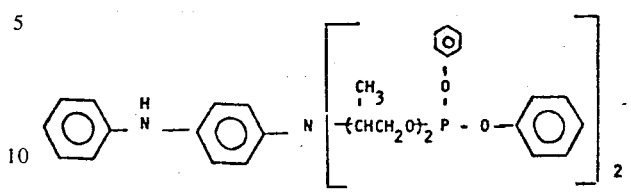

a. 8105 grams of p-aminodiphenylamine were charged to a pressure reactor and heated to 101°C under a vacuum of 29 inches of mercury. The reactor was then sealed and 11.3 pounds (5130 grams) of propylene oxide were fed to the reactor over a 2 hour and 38 minute period at temperatures up to 146.2°C and pressures up to 18 psig. The reaction mixture was thereafter stirred for an additional 17 minutes during which time the pressure in the reactor dropped to zero psig. The reactor was then opened and 40.5 grams of anhydrous sodium acetate were added. The reactor was again sealed and an additional 11.3 pounds of propylene oxide were fed thereto over a 2 hour and 4 minute period at temperatures of 148.8°–157.5°C and pressures up to 23 psig. An additional 12 minute stirring period was required to digest the propylene oxide to zero psig.

The product was a dark liquid whose viscosity was found to be 26,000 poises at 25.7°C. The weight per gallon of this material was 9.03 pounds (902 gms/liter), the primary amine content was nil, the secondary amine content was found to be 0.16 milliequivalents per gram of sample while the tertiary amine content was found to be 2.32 milliequivalents per gram of sample. The product contained 4 moles of propylene oxide per mole of p-aminodiphenylamine.

b. 205 grams of the above propoxylated p-aminodiphenylamine product of (a) and 310.3 grams of triphenylphosphite were charged to a 1 liter flask equipped with a nitrogen gas inlet, thermometer with thermowatch, distillation head with straight steam jacketed condenser, glass connector with a vacuum takeoff and a 500 milliliter receiver. The reactants in the flask were heated under a nitrogen atmosphere to 103°C and vacuum was applied. The reaction mixture was maintained at 193.2°–194°C and 0.11 to 4.5 mm mercury pressure for 31 minutes. The reaction flask was weighed and a 105.1 gram weight loss was recorded. The final product was a dark viscous liquid.

EXAMPLE 2

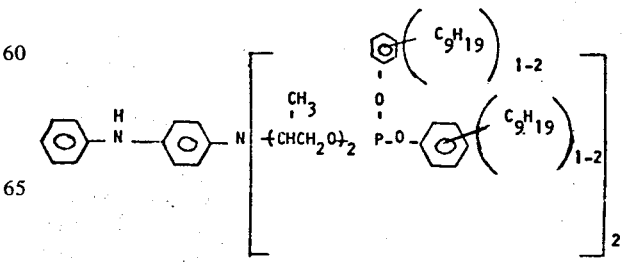

63.6 grams of a proxylated p-amino diphenylamine, was prepared from distilled p-aminodiphenylamine by the procedure of part (a) of Example 1, was charged to a 500 milliliter reaction flask, equipped as in part (b) of Example 1, for reaction with a phosphite. The propoxylated amine used in this example was light in color and exhibited a total amine value of 2.37 milliequivalents per gram of sample, a nil primary and secondary amine content and a tertiary amine level of 2.33 milliequivalents per gram of sample. 212.1 grams of tri(mixed mono-dinonyl) phenylphosphite were also charged into the reaction flask. The mixture was heated to 44.5°C and vacuum was applied. The reaction mixture was heated to 192°C over a 4 hour period and pressure in the reaction vessel was reduced to less than 0.1 mm mercury pressure. The mixture was held at less than 0.1 mm mercury pressure and at a temperature of from 191.2°–192°C for an additional 41 minutes. The reaction flask was weighed and a weight loss of 68.9 grams was recorded. The final product was a straw colored viscous liquid.

EXAMPLE 3

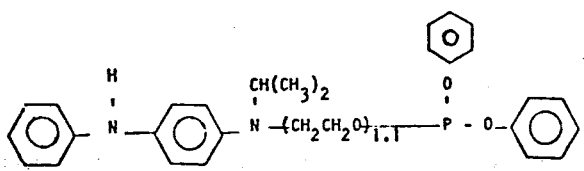

a. 410.0 grams of N-isopropyl-N'-phenyl-p-phenylenediamine were charged to a 1 liter pressure reactor and, by the procedure of part (a) of Example 1, 88 grams of ethylene oxide were added thereto over a period of 11 minutes at a temperature of 141°–156°C. and pressure of up to 79 psig. The reaction mixture was maintained at 146°–155°C., with agitation, for an additional 92 minutes until the pressure gauge indicated a zero pressure. The product, after cooling, was a dark viscous liquid which showed signs of crystallization or partial solidification after a prolonged storage (5 months). Analysis of the product indicated a nil primary amine content, 0.20 milliequivalents per gram of sample of secondary amine and 3.31 milliequivalents per gram of sample of tertiary amine.

b. 105.9 grams of the above product and 41.4 grams of triphenylphosphite were charged to a 250 millileter reaction flask equipped as in part (b) of Example 1. The reaction mixture was heated under vacuum (0.35–0.4 mm mercury pressure) to 149°C over a 116 minute period. The reaction mixture was then held at 149° to 154°C and 0.3–0.4 mm mercury pressure for an additional 93 minute period. The reaction vessel was weighed and a 34.6 gram weight loss was recorded. The final product was a solid melting in the 94°–106°C range.

EXAMPLE 4

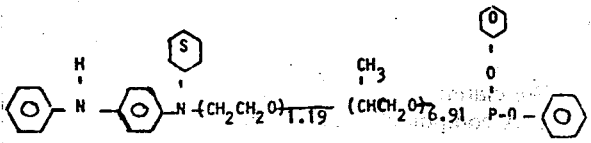

476.7 grams by weight of N-phenyl-N'-cyclohexyl-p-phenylenediamine was charged, under vacuum, to a 1 liter pressure reactor and heated to 100°C. The reactor was sealed and the amine was further heated to 156°C with agitation. 94 grams by weight of ethylene oxide was added over an 18-minute period at a reaction temperature of 146°–⅝°C and reaction pressures of up to 102 psig. The reaction mixture was then allowed to stir for an additional 2 hours and 14 minutes at 146°–156°C until the pressure gauge indicated zero pressure. The final product, after cooling, was a dark very thick paste exhibiting a nil primary and secondary amine content and a tertiary amine level of 2.88 milli-equivalents per gram of sample. 343.5 grams of the above oxyethylated N-phenyl-N'-cyclohexyl-p-phenylenediamine product and 3.4 grams of sodium methoxiole were charged to a 1 liter flask equipped with a 500 milliliter pressure equalized dropping funnel, nitrogen gas inlet, mechanical agitator, thermometer with thermowatch and dual water cooled condensers. Air cooling actuated by a solenoid valve attached to the thermowatch was used to maintain temperatures below 180°C. The amine was initially heated to 172°C, under a nitrogen gas atmosphere, and 433.7 grams by weight of propylene oxide were added over a period of 10 hours and 10 minutes to avoid excessive refluxing. The product, after cooling, was a dark liquid exhibiting a nil primary and secondary amine content and a tertiary amine content of 1.36 milli-equivalents per gram of sample.

108 grams of the second above product and 15.5 grams of triphenylphosphite were charged to a suitable reactor under vacuum (0.1 mm mercury and less) to 146°C over a 38 minute period. Distillation had occurred during this period. The reaction mixture was then held for an additional 54 minute period at 144.5–146°C and 0.045–0.07 mm mercury pressure. A weight loss of 14.3 grams in the reaction mixture was recorded. The final product was a liquid with a viscosity of 217,800 centipoises at 23°C.

In a manner similar to the above processes of Examples 1–4, the appropriate oxyalkylenated - aminodiphenylamine intermediate may be made by the process of U.S. Pat. No. 3,330,777 and in turn reacted with a selected, substituted or unsubstituted, trialkyl or triaryl phosphite to produce the compounds of the instant invention.

EXAMPLE 5 a. The product of Example 2 was evaluated for antidegradant properties, by comparison with the commercial antidegradant additives Santoflex 13 and Agerite Resin D, in a typical rubber formulation. Santoflex 13 is an N-(1,3-dimethylbutyl)-N'-phenyl-p-phenylenediamine produced by Monsanto Chemical Corporation and Agerite Resin D is a polymerized 1,2-dihydro-2,2,4-trimethylquinoline produced by R. T. Vanderbilt Company. A master batch was prepared and Banbury mixed containing the following components.

| | Parts by Weight |
|---|---|
| Natural Rubber (Grade No. 1 RSS) | 60 |
| SBR (Grade No. 1502) | 40 |
| Stearic Acid | 1 |
| Zinc Oxide | 5 |
| Carbon Black | 50 |

The so mixed master batch was divided into 1404 gram samples. A 9 gram quantity of the antioxidant to be evaluated was added to the requisite samples, with the exclusion of the control, and each sample was further Banbury mixed at 220° Fahrenheit. Accelerators, 10.8 grams of benzothiazyl disulfide and 18.0 grams of sulfur, were then added to each sample which was then milled at 160°Fahrenheit to produce the final test samples.

b. Test samples prepared in part (a) were brought to the point of optimum cure at a temperature of 320° Fahrenheit. The physical properties of the so cured test samples were then measured, by standard methods, with the results as indicated in Table 1.

TABLE I

| Antioxidant | % Elongation | 100% Modules (psi) | 200% Modules (psi) | 300% Modules (psi) | Tensile (psi) | Hardness |
|---|---|---|---|---|---|---|
| Santoflex 13 | 460 | 310 | 1030 | 2070 | 3320 | 65 |
| Agerite Resin D | 420 | 350 | 1040 | 2080 | 3160 | 66 |
| Control | 440 | 340 | 980 | 1940 | 3170 | 66 |
| Prod. of Ex. 2 | 420 | 310 | 980 | 1930 | 2960 | 63 |

TABLE II

| Antioxidant | % Elongation | 100% Modules | 200% Modules | Tensile (psi) | Hardness |
|---|---|---|---|---|---|
| Santoflex 13 | 390 | 360 | 1130 | 2980 | 63 |
| Agerite Resin D | 380 | 410 | 1120 | 2900 | 65 |
| Control | 420 | 380 | 1020 | 3110 | 65 |
| Prod. of Ex. 2 | 410 | 390 | 1020 | 2900 | 65 | c. Test samples of part (a) were cured for 21 minutes at 320° Farenheit and measured for physical properties with results as indicated in Table II.

d. Test samples, cured as in part (c) were subjected to an oxygen atmosphere of 300 psi at 158° F for 22 hours with the affect on physical properties as shown in Table III.

TABLE III

| Antixodiant | % Elongation | 100% Mod. (psi) | 200% Mod. (psi) | 300% Mod. (psi) | Tensile (psi) | Hardness |
|---|---|---|---|---|---|---|
| Santoflex 13 | 300 | 510 | 1415 | 2410 | 2460 | 65 |
| Agerite Resin D | 280 | 540 | 1470 | — | 2385 | 65 |
| Control | 250 | 530 | 1235 | — | 1700 | 68 |
| Prod. of Ex. 2 | 310 | 465 | 1280 | 2170 | 2290 | 65 |

TABLE IV

| Antioxidant | % Elongation | 100% Mod. | 200% Mod. | 300% Mod. | Tensile | Hardness |
|---|---|---|---|---|---|---|
| Santoflex 13 | 320 | 470 | 1315 | 2470 | 2840 | 70 |
| Agerite Resin D | 330 | 430 | 1405 | 2260 | 2810 | 70 |
| Control | 340 | 410 | 1210 | 2410 | 2660 | 70 |
| Prod. of Ex. 2 | 360 | 390 | 1120 | 2270 | 2830 | 66 | e. Test samples, cured as in part (c) were subjected to weather simulation testing wherein the samples were subjected to 100 hours, at 20% elongation, of alternating ultra violet radiation and rain cycles. The effect on physical properties is shown in Table IV.

f. Samples, cured as in (a), were subjected to a whitewall satin test by curing them together with a thin coating of whitewall tire stock. After curing the whitewall clad samples were exposed in ultraviolet light on a white surface for 2½ and 48 hours and thereafter the whitewall tire stock was evaluated for discoloration. The results as indicated in Table V.

TABLE V

| Antioxidant | 2½ hrs. | 48 hrs. | Code |
|---|---|---|---|
| Santoflex 13 | 4 | 5 | 0—No staining |
| Agerite Resin D | 1 | 2 | 1—Very slight |
| Control | 0 | 1 | 2—Slight |
| Prod. of Ex. 2 | 1 | 1 | 3—Medium |
|  |  |  | 4—Medium dark |
|  |  |  | 5—Dark | g. Samples, cured as in part (c) were subjected to contact and migration stain testing. A square of the sample was placed in a white enamel plate and the sample containing plate was exposed to ultraviolet light for 48 hours. The sample was removed and the enameled plate in direct contrast therewith was evaluated, by the code of (f), for staining thereon. Migration stain was determined by evaluating the enameled plate area in the periphery of contact of the sample by the code of (f). The results are in Table VI.

TABLE VI

| Antioxidant | Contact Stain | Migration Stain |
|---|---|---|
| Santoflex 13 | 1 | 3 |
| Agerite Resin D | 1 | 0 |
| Control | 0 | 0 |
| Prod. of Ex. 2 | 0 | 0 |

We claim:
1. A compound of the formula

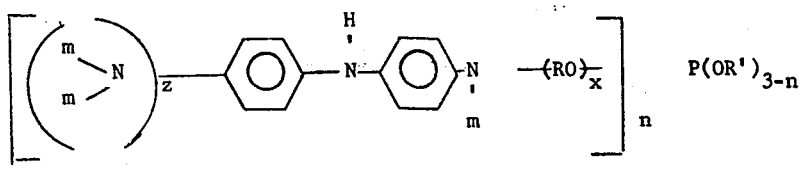

wherein
- R is selected from the group consisting of ethylene, 1,2 propylene, 1,2 butylene, 2,3 butylene, styrylene and mixtures thereof,
- x is an integer from 1 to 12,
- R' is selected from the group consisting of alkyl substituted or unsubstituted phenyl and alkyl of 1 to 18 carbon atoms,
- n is an integer from 1 to 3,
- each m is a member, selected independently from the group consisting of alkyl and cycloalkyl of up to 20 carbon atoms, $(RO)_{\overline{x}}H$ and $(-(RO)_{\overline{x}})_n$ $P(OR')_{3-n}$, wherein R, R', n and x are as above described, and
- z is 0 or 1, providing that when z is 0,

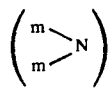

Z is hydrogen.

2. A compound of claim 1 wherein z is 0.

3. A compound of claim 1 wherein R' is alkyl substituted phenyl or phenyl.

4. A compound of claim 1 wherein m is $(-(RO)_{\overline{x}})_n P(OR')_{3-n}$ and z is 0.

5. A compound of claim 1 wherein m is alkyl of 1–20 carbon atoms.

6. A compound of claim 3 wherein m is cyclohexyl.

7. A compound of claim 1 of the formula.

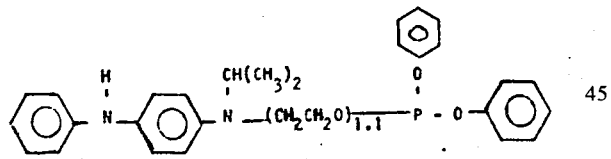

8. A compound of claim 1 of the formula

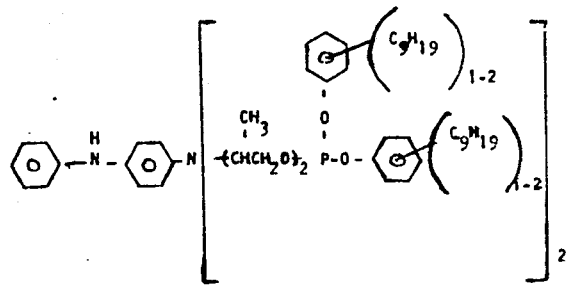

9. A compound of claim 1 of the formula

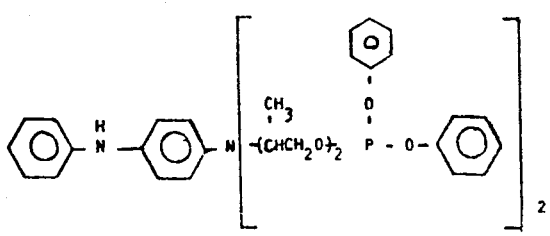

10. A compound of claim 1 of the formula

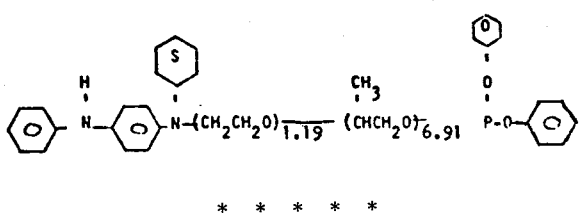

* * * * *

UNITED STATES PATENT OFFICE
CERTIFICATE OF CORRECTION

PATENT NO. : 3,956,428
DATED : May 11, 1976
INVENTOR(S) : D. Bruce Merrifield, Joseph A. Pawlak & James G. Colson It is certified that error appears in the above—identified patent and that said Letters Patent are hereby corrected as shown below:

Column 2, line 21, "m is an integer" should read ---n is an integer---. Column 3, line 26, "discloring" should read ---discoloring---; line 65, "sub-atmoshperic" should read ---sub-atmospheric---. Column 5, line 1, "proxylated" should read ---propoxylated---. Column 6, line 7, "146-3/8°C" should read ---146-156°C---. Column 7, line 63, "satin" should read ---stain---.

Signed and Sealed this

Fifteenth Day of March 1977

[SEAL]

Attest:

RUTH C. MASON
Attesting Officer

C. MARSHALL DANN
Commissioner of Patents and Trademarks